US009591993B2

(12) United States Patent
Morris Bamberg et al.

(10) Patent No.: US 9,591,993 B2
(45) Date of Patent: Mar. 14, 2017

(54) METHOD AND SYSTEM FOR ANALYZING GAIT AND PROVIDING REAL-TIME FEEDBACK ON GAIT ASYMMETRY

(75) Inventors: Stacy J. Morris Bamberg, Salt Lake City, UT (US); Randy J. Carson, Salt Lake City, UT (US); Joseph B. Webster, Salt Lake City, UT (US); Dante Bertelli, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 208 days.

(21) Appl. No.: 12/407,967

(22) Filed: Mar. 20, 2009

(65) Prior Publication Data

US 2009/0240171 A1 Sep. 24, 2009

Related U.S. Application Data

(60) Provisional application No. 61/070,412, filed on Mar. 20, 2008.

(51) Int. Cl.

| | |
|---|---|
| ***A61B 5/103*** | (2006.01) |
| ***A61B 5/117*** | (2016.01) |
| *A61B 5/00* | (2006.01) |
| *A61B 5/11* | (2006.01) |
| *A43B 3/00* | (2006.01) |

(52) U.S. Cl.

CPC ............ *A61B 5/1038* (2013.01); *A61B 5/486* (2013.01); *A43B 3/0005* (2013.01); *A61B 5/112* (2013.01); *A61B 5/1123* (2013.01); *A61B 5/6807* (2013.01); *A61B 5/6829* (2013.01)

(58) Field of Classification Search

CPC ..... A61B 5/1038; A61B 5/112; A61B 5/1123; A61B 5/6807; A61B 5/6829; A43B 3/0005

USPC ......... 600/587, 592, 595; 482/8, 9; 702/160; 73/379.01; 377/24.2

See application file for complete search history.

(56) References Cited

U.S. PATENT DOCUMENTS

| | | | | |
|---|---|---|---|---|
| 4,745,930 | A | | 5/1988 | Confer |
| 5,323,650 | A | | 6/1994 | Fullen et al. |
| 5,408,873 | A | | 4/1995 | Schmidt et al. |
| 5,437,289 | A | | 8/1995 | Liverance et al. |
| 5,471,405 | A | * | 11/1995 | Marsh ............................ 702/41 |
| 5,586,557 | A | | 12/1996 | Nelson et al. |
| 5,655,316 | A | | 8/1997 | Huang |
| 5,875,571 | A | | 3/1999 | Huang |
| 5,878,378 | A | | 3/1999 | Brommer et al. |

(Continued)

FOREIGN PATENT DOCUMENTS

| | | |
|---|---|---|
| WO | WO 2005/094679 | 10/2005 |
| WO | WO 2008/058048 | 5/2008 |

OTHER PUBLICATIONS

Urry, Stephen, "Plantar pressure-measurement sensors," Meas. Sci. Technol.,1999, 1 page abstract only.

(Continued)

*Primary Examiner* — Devin Henson

(74) *Attorney, Agent, or Firm* — Workman Nydegger

(57) ABSTRACT

A method and system for analyzing gait asymmetry between left and right feet of individuals by measuring and comparing stance phase time and/or stance phase force between left and right feet during gait, and providing real-time sensory feedback if stance phase time/force inequality exceeds a predetermined threshold.

22 Claims, 4 Drawing Sheets

(56) References Cited

U.S. PATENT DOCUMENTS

| | | | | |
|---|---|---|---|---|
| 5,925,000 | A | 7/1999 | Marciniak et al. | |
| 5,929,332 | A | 7/1999 | Brown | |
| 6,018,705 | A | 1/2000 | Gaudet et al. | |
| 6,031,463 | A | 2/2000 | Bechmann | |
| 6,122,846 | A | 9/2000 | Gray et al. | |
| 6,186,000 | B1 | 2/2001 | Kaneko et al. | |
| 6,195,921 | B1 | 3/2001 | Truong | |
| 6,273,863 | B1 | 8/2001 | Avni et al. | |
| 6,360,597 | B1 * | 3/2002 | Hubbard, Jr. | A43B 3/00 73/172 |
| 6,408,545 | B1 | 6/2002 | Song | |
| 6,611,789 | B1 | 8/2003 | Darley | |
| 6,658,079 | B1 * | 12/2003 | Macklin et al. | 377/24.2 |
| 6,807,869 | B2 * | 10/2004 | Farringdon et al. | 73/862.046 |
| 6,876,947 | B1 | 4/2005 | Darley et al. | |
| 6,898,550 | B1 | 5/2005 | Blackadar et al. | |
| 7,191,644 | B2 | 3/2007 | Haselhurst et al. | |
| 7,225,565 | B2 | 6/2007 | DiBenedetto et al. | |
| 7,355,519 | B2 * | 4/2008 | Grold et al. | 340/573.7 |
| 7,610,813 | B2 * | 11/2009 | Hughes | A61B 5/0002 73/760 |
| 7,648,441 | B2 * | 1/2010 | Silk | A61B 5/1038 482/1 |
| 7,758,523 | B2 * | 7/2010 | Collings et al. | 600/592 |
| 7,827,000 | B2 * | 11/2010 | Stirling et al. | 702/141 |
| 7,878,990 | B2 * | 2/2011 | Al-Obaidi et al. | 600/592 |
| 8,055,469 | B2 * | 11/2011 | Kulach | A63B 24/0062 702/141 |
| 2007/0202478 | A1 * | 8/2007 | Al-Obaidi et al. | 434/247 |
| 2007/0204687 | A1 | 9/2007 | Haselhurst et al. | |
| 2008/0108913 | A1 | 5/2008 | Lengsfeld et al. | |
| 2008/0167580 | A1 * | 7/2008 | Avni et al. | 600/587 |

OTHER PUBLICATIONS

Bamberg, Stacy J Morris et al., "Gait analysis using a shoe-integrated wireless sensor system," IEEE, Transactions on Information Technology in Biomedicine, Jul. 2008, vol. 12, No. 4. pp. 413-423.

http://www.tgdaily.com, Gruener, Wolfgang, "MIT develops iShoe to keep you on your feet," Jul. 16, 2008, 1 page.

Trafton, Anne, "Balance problems? Step into the iShoe, MIT grad students' invention could one day prevent falls" Jul. 16, 2008, 2 pages.

Lindsay, Jay "Astronaut technology could prevent elderly falls insole sensors read how well a person is balancing, provide info to doctor," Jul. 31, 2008, 4 pages.

Perttunen, J.R. et al., "Gait asymmetry in patients with limb length discrepancy," Scand J. Med Sci Sports, 2004: vol. 14, pp. 49-56.

Perry, Stephen et al., "Efficacy and effectiveness of a balance-enhancing insole," Journal of Gerontology: Medical Sciences, vol. 63A, No. 6, pp. 595-602.

Granat, M.H. et al., "A body-worn gait analysis system for evaluating hemiplegic gait," 1995, Med. Eng. Phys. vol. 17, No. 5, pp. 390-394.

Ming-Yih Lee et al., "Design of a new biofeedback proprioceptive neuromuscular facilitation system for below-knee amputees," Biomed Engineering Applications, basis and communications, 2006, vol. 18, No. 4. pp. 109-197.

Rodgers, Mary et al., "Effects of gait velocity on COP symmetry measures in individuals with stroke," http://pt.umaryland.edu, 2 pages.

Harris-Love, Michelle et al., "Hemiparetic gait parameters in overground versus treadmill walking," Neurorehabilitation and Neural Repair, 2001, vol. 15, pp. 105-112.

Mattes, Sarah et al., "Walking symmetry and energy cost in persons with unilateral transtibial amputations: matching prosthetic and intact limb inertial properties," Arch Phys Med Rehabil. May 2000, vol. 81 pp. 561-568.

Novak, Peter, "Effect of step-synchronized vibration stimulation of soles on gait in parkinson's disease: a pilot study," May 4, 2006, Journal of NeuroEngineering and Rehabilitation, vol. 3, No. 9, 7 pages.

Mizelle, Chris et al., "Center of pressure measures predict hemiparetic gait velocity," ISB XXth Congress—ASB 29th Annual Meeting, Jul. 31-Aug. 5, Cleveland, Ohio, 1 page.

Kimmeskamp, S. et al., "Analysis of plantar pressures during gait of patients with parkinson's disease," Germany 2 pages.

Surdilovic, Dragoljub et al., "Gait phase and centre of pressure measuring system," IEEE, 2004, pp. 331-334.

Bamberg, Stacy J. Morris, "A shoe-integrated sensor system for wireless gait analysis and real-time therapeutic feedback," Jun. 2004, Thesis 314 pages.

Limits on the Measurement of Activity Level in Children Using Ultrasound and Photoelectric Cells, www.eric.ed.gov/ERICWebPortal/custom/portlets/recordDetails/detailmini.jsp?_nfpb=true . . . 1972, 2 pages.

Eaton, Warren, "Measuring Activity Level with Actometers: Reliability, Validity, and Arm Length" Child Development, 1983. 54, 720-726, (1 page).

Duncan, Michael, "Pedometer determined physical activity levels in primary school children from central England" Preventive Medicine, May 2007, vol. 44, Issue 5, pp. 416-420 (2 pages).

Roberts, Dawn E., "Measurement of physical activity with accelerometers in children," 2007, Scholarworks@UMass Amherst, http://scholarworks.umass.edu/dissertations/AAI3254924/, abstract only.

Tryon Warren, "Measuring activity using actometers: A methodological study," Journal of Psychopathology and Behavioral Assessment, Jun. 1984, vol. 6. No. 2 abstract only.

Jelen Piotr et al., "Expressing gait-line symmetry in able-bodied gait," Dynamic Medicine, BioMed Central, Dec. 19, 2008, 9 pages.

Bamberg, et al., "Toward In-shoe motion analysis and activity monitoring: Detecting incline during walking gait," 1 page, abstract, May 2007.

Zhang, Kuan et al., "Assessment of human locomotion by using an insole measurement system and artificial neural networks," Journal of Biomechanics, 2005, 38 pp. 2276-2287.

Bamberg et al., "Toward in-shoe motion analysis and activity monitoring: detecting incline during walking gait," poster, BMES conference, Sep. 27, 2007, 1 page.

Bamberg et al., "An interactive auditory feedback system to improve gait symmetry in persons with amputations," 1 page.

Paradiso, Joseph et al., "Interactive therapy with instrumented footwear," Apr. 24-29, 2004, Vienna Austria, 3 pages.

Bamberg, Stacy J. Morris et al., "Development of a quantitative in-shoe measurement system for assessing balance: sixteen-sensor insoles," IEEE, EMBS Annual International Conference, Aug. 30, 2006-Sep. 3, 2006.

* cited by examiner

METHOD AND SYSTEM FOR ANALYZING GAIT AND PROVIDING REAL-TIME FEEDBACK ON GAIT ASYMMETRY

PRIORITY CLAIM

Priority is claimed to U.S. Provisional Patent Application Ser. No. 61/070,412, filed on Mar. 20, 2008, which is hereby incorporated herein by reference in its entirety.

BACKGROUND

Field of the Invention

The present invention relates generally to gait assist devices.

Related Art

Asymmetry of gait refers to a difference in gait parameters between the left and right lower limbs, including both asymmetrical distribution of weight, as well as unequal time spent on the left and right feet during stance. Asymmetric gait is common in individuals with unilateral lower limb amputations, post cerebral accident victims, stroke victims, and lower limb orthopedic surgery patients. Asymmetric gait has been linked with chronic overloading in the non-amputated limb. Such overloading can occur because less time is often spent on the amputated leg and a shorter step length is often taken on the intact leg. Additionally, gait asymmetry has been shown to increase with walking speed which can account for greater loading of the joints in the intact limb of unilateral amputees.

This asymmetry of gait and subsequent overloading of the non-amputated limb has been associated with osteoarthritis in the knee of the non-amputated limb, which can have a profound impact on an individual's quality of life. Research suggests this higher prevalence of osteoarthritis may be due to the increased force in the intact leg which results from asymmetrical gait. A possible explanation for the asymmetric force is the lack of proprioceptive feedback provided through the prosthetic as compared to the normal biological ankle. Unfortunately, interventions to improve gait symmetry in the amputee population have historically been qualitative and have focused on descriptions of symptoms resulting from asymmetrical gait instead of possible preventive therapy or treatment.

SUMMARY OF THE INVENTION

The inventors of the present invention have recognized that it would be advantageous to develop a method and/or system for analyzing gait asymmetry (between left and right feet) of individuals, such as unilateral lower limb amputees, post cerebral accident victims, stroke victims, or lower limb orthopedic surgery patients, by measuring and comparing stance phase time and/or stance phase force between left and right feet during gait, and providing real-time sensory feedback if stance phase time/force inequality exceeds a predetermined threshold.

The inventors of the present invention have recognized that it would be advantageous to develop a method and device for evaluating the asymmetry of gait of a user and providing feedback in real time if the asymmetry is over a specified threshold to allow lower extremity amputees to identify and correct gait asymmetries. Additionally, the inventors of the present invention have recognized that it would be advantageous to develop a method and device to detect the amount of time an individual spends on their left foot compared to their right foot to detect asymmetry of stance time or a limp, and to provide real time feedback if the asymmetry is over a specified threshold. Additionally, the inventors of the present invention have recognized that it would be advantageous to develop a method and device to detect changes in total force between the two feet to detect asymmetry of stance loading, and to provide real time feedback if the asymmetry is over a specified threshold. Moreover, the inventors of the present invention have recognized that it would be advantageous to develop a method and device that will measure stance phase times and applied loading through force sensors coupled to an electronic processor that will determine if a gait asymmetry exists and provide feedback to the user via the electronic processor. Furthermore, the inventors of the present invention have recognized that it would be advantageous to develop a method and device to analyze stance phase force symmetries, stance phase times, bilateral forces, and degree of asymmetry.

The invention provides a method for analyzing gait and providing real time feedback on gait asymmetry. Sensor data is received from a plurality of sensors disposed within left and right shoes when the shoes are moved through gait motions by a user of the shoes. The sensor data is analyzed with an electronic processor by comparing sensor data from the left shoe to the right shoe to determine a difference between the left and right shoes. A sensory feedback alarm is activated to alert the user when the difference between the left and right shoes exceeds a predetermined threshold. In accordance with one aspect of the present invention, stance phase times or stance phase forces or both of the left and right shoes are determined and compared based on the sensor data.

In addition, the invention presents a method for analyzing gait and providing real time feedback on gait asymmetry. Sensor data is received from a plurality of sensors disposed within left and right shoes when the shoes are moved through gait motions by a user of the shoes. Stance phase times or stance phase forces or both of the left and right shoes are determined and compared with an electronic processor based on the sensor data. A difference between stance phase time or stance phase forces or both between the left and right shoes is determined. A sensory feedback alarm is activated to alert the user when the difference of the stance phase times or stance phase forces or both of the left and right shoes exceed a predetermined threshold.

Furthermore, the invention presents lower extremity feedback system with a plurality of sensors associated with left and right shoes. A microcontroller is electronically coupled to the plurality of sensors and capable of analyzing data from the sensors to determine and compare stance phase times or stance phase forces or both of the left and right shoes during gaited motion; and to determine a difference between stance phase times or stance phase forces or both of the left and right shoes. A sensory feedback device is electronically coupled to the microcontroller to sound a sensory alarm when the difference between stance phase times or stance phase forces or both of the left and right shoes exceeds a predetermined threshold.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
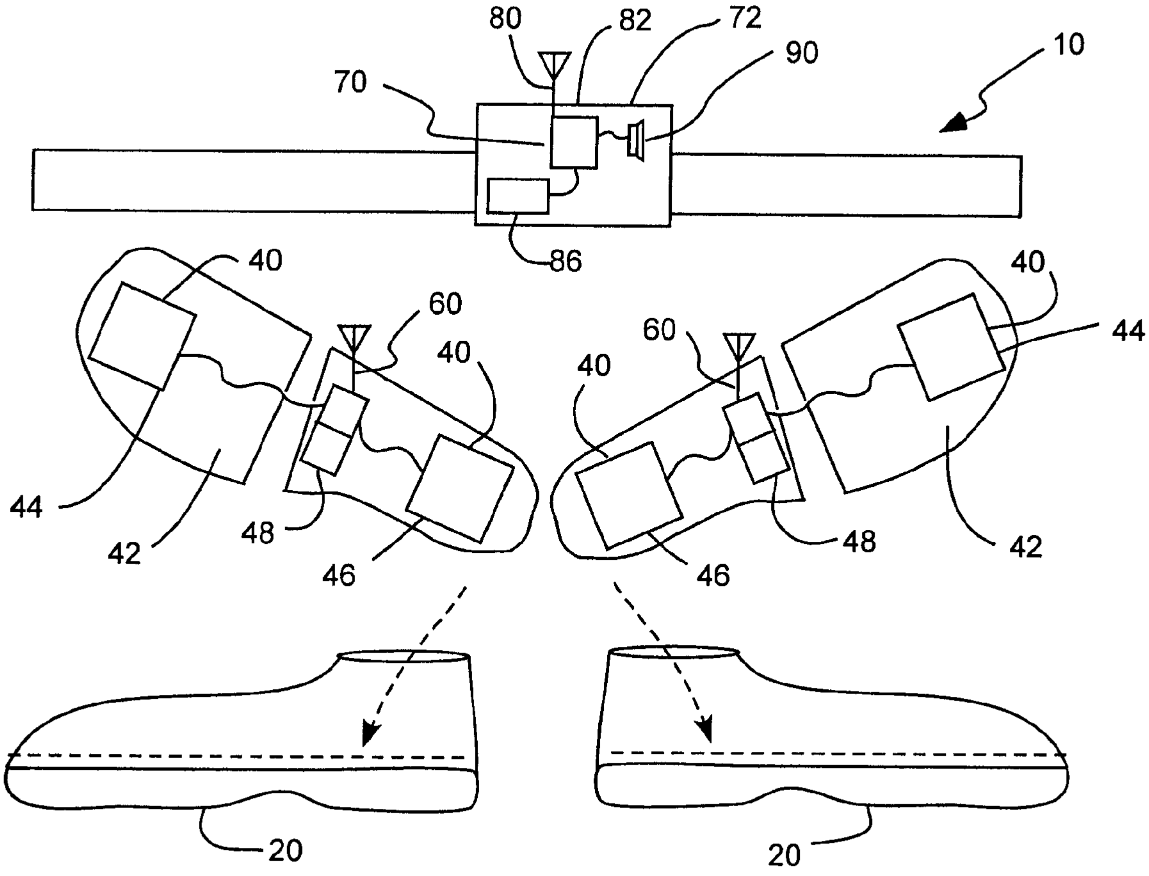
FIG. 1 is a schematic view of a lower extremity feedback system in accordance with an embodiment of the present invention, shown associated with shoes worn by a user.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The embodiments of the present invention described herein provide for a lower extremity feedback system and method that evaluate the asymmetry of gait of the user and provide real time feedback if the asymmetry is over a specified threshold. The lower extremity feedback system can include a pair of instrumented shoes and a feedback device. In one aspect, the shoes can be foot-worn monitors that can include multi-sensor insoles. The terms “shoe” and “shoes” are used broadly herein to mean any footwear, whether commercially available or custom made for carrying the sensors, such as shoes, sneakers, boots, sandals, slippers, athletic footwear, socks, prosthetic foot or shell of a prosthetic foot, etc. The shoes can include a plurality of sensors that can be placed under the insole of the shoes and arranged to measure the force distribution from the time the heel strikes the floor until the time the last toe is off the floor. The sensors in the shoe can be operatively coupled to an electronic processor, such as via a wireless transmitter and receiver. The electronic processor can be coupled a feedback alarm. The electronic processor can collect data measured by the plurality of sensors in each shoe and control feedback by way of the feedback alarm. The electronic processor can analyze the data to determine the degree of asymmetry between the shoes during gait. When the degree of symmetry falls below a predetermined threshold, the feedback alarm will be activated.

As illustrated in FIG. 1, a lower extremity feedback system, indicated generally at 10, in accordance with the present invention is shown for use in evaluating the asymmetry of gait of a user and providing real time feedback if the asymmetry is over a predetermined threshold. The lower extremity feedback system can include a pair of shoes, or left and right shoes 20; a plurality of sensors 40 associated with and carried by the shoes; an electronic processor 70 operatively coupled to the sensors via a wireless transmitter 60 and receiver 80; and a feedback device 90, such as a transducer or speaker. The feedback device could also provide tactile feedback, such as vibration, or visual feedback, such as lights or a display.

The pair of shoes 20 can be an ordinary pair of shoes or boots as known in the art. For example, the shoes can be sneakers that can be worn on a natural foot or a prosthetic foot of the user. In one aspect of the present invention, the sensors can be configured to be disposed in commercially available shoes already obtained by the user, such as with a sensor insert or insole 42. Alternatively, the sensors can be provided in a custom shoe or foot-borne device specifically made for the sensors and/or user. The insole 42 can be a plastic or rubber insert formed around the sensors 40. The insert 42 can be sized and shaped to fit within the shoe under the user’s foot or under the insole. In another aspect, the insert 42 can replace the insole of the shoe. The insole 42 can position toe sensors 44 in the toe of the shoe 20 and heel sensors 46 in the heel of the shoe. Additionally, other sensors can be placed in the arch or ball location of the sole if desired. Furthermore, other circuitry, electronics and/or batteries 48 can be places in the insoles. The insoles can be split, as shown, to help place the toe sensors at the toe, and heel sensors at the heel.

The sensors 40 can include force sensors, bilateral force sensors, strain gages, accelerometers, pedometers, and levels. Additionally, combinations of these types of sensors can be used in order to measure a wide variety of dynamic environmental conditions during the gaited motion of the user. Other sensors, as known in the art, can also be used.

The sensors 40 are operatively coupled to the electronic processor 70, such as by wireless transmitter 60 and receiver 80. In one aspect, the transmitter can be a wireless data transmitter that can transmit a wireless signal such as a RF signal, an ultra-violet signal, an ultra-sonic signal, an infrared signal, and an optical signal. The transmitter can transmit data from the sensors to the data receiver 80 associated with the processor 70. The data receiver can receive the sensor data transmitted from the data transmitter. The receiver can be a wireless data receiver that can be locatable in a remote location from the wireless transmitter. For example, the wireless receiver can be located in a waist pack 72 that can be attached to the shoe wearer’s waist. Additionally, the wireless receiver can be located in a computer. The data receiver can route the sensor data to the electronic processor. In one aspect of the present invention, the data processor can be located remote from the sensors and/or shoes, such as on a hip or belt worn housing. Alternatively, the data processor can be located in or on the shoe, or around the ankle or prosthesis. Alternatively, the processor and sensors can be formed together on a circuit within the shoe or insole. Alternatively, the processor can be located in a wrist-worn device or in a housing that can be put in a pocket.

The electronic processor 70 can process the sensor data received from the sensors. The electronic processor 70 can include a computer, a microprocessor, a microcontroller, and the like. The electronic processor can include electronic memory storage as known in the art. Additionally the electronic processor can be powered by a battery power source 86.

The electronic processor 70 can analyze the sensor data for asymmetry. For example, the electronic processor 70 can compare the sensor data from one of the pair of shoes to the other of the pair of shoes in order to determine the difference or asymmetry between each of the shoes. In one aspect, the electronic processor 70 can compare the stance phase time of one of the shoes with the stance phase time of the other of the shoes in order to determine the stance phase time asymmetry of the user. As used in this application, stance phase time is the time the user applies a force to one of the shoes.

In another aspect, the electronic processor 70 can compare the total stance phase force applied to one of the shoes with the total stance phase force applied to the other of the shoes in order to determine the stance phase force asymmetry of the user. In yet another aspect, the electronic processor 70 can determine both the stance phase time asymmetry and the stance phase force asymmetry. The electronic processor can compare the sensor data from the shoes, and determine any difference in real time, during gait motion or while the user is walking.

In all these aspects, the electronic processor 70 can compare the stance phase time asymmetry, the stance phase force loading asymmetry, and/or a combination of the asymmetries with preprogrammed and predetermined thresholds in order to determine if the asymmetries exceed the threshold. If the asymmetries or combination of asymmetries exceed the predetermined threshold, the electronic processor 70 can activate the feedback device 90.

It will be appreciated that the asymmetry thresholds can be determined for any specific individual user or the thresholds can be based on data collected from a statistical population. If the thresholds are based on a specific individual, prior testing and data collection with the individual wearing the pair of shoed can be conducted in order to determine a baseline of performance during the gait of the user. The baseline can then be used to calculate the thresholds. The predetermined threshold can be at least 15% difference between the left and right shoes.

The feedback device 90 can be electronically coupled to the electronic processor 70 and can provide real time feedback to the user. The feedback device 90 can be an alarm that can signal to the user when the user's gait is outside the predetermined threshold. In this way, the user can adjust his or her gait stance and loading to correct the asymmetrical condition. Advantageously, correcting the gait in real time reduces the undesirable loading on the joints of user thereby reducing the likelihood of osteoarthritis forming in the joints.

In one aspect, the feedback device 90 can include an audible alarm that can be emitted from a speaker. The audible alarm can give auditory cues to the wearer of the shoes during walking. The auditory alarm can produce a separate and distinct sound for each of a variety of gait asymmetry conditions. For example, in the event the stance phase time asymmetry exceeds the predetermined threshold the auditory alarm can sound a first distinct sound that will alert the user of the shoes to the phase time asymmetry condition. Similarly, in the event the stance phase force loading asymmetry exceeds the predetermined threshold, the auditory alarm can produce another second distinct sound that is different than the sound used to alert the user to the stance phase time asymmetry, in order to alert the user to the stance phase force loading asymmetry. Additionally, another separate and third distinct sound can be used to alert the user to a combined stance phase time and force loading asymmetry. Furthermore, the auditory alarm can also produce a different sound to alert the user when the user's gait is within an acceptable asymmetry range so as to train the user how it feels to walk or run in an acceptable symmetrical condition.

In another aspect, the feedback device 90 can include other proprioceptive alarms. For example, the feedback device can include an audio indicator, a visual indicator, and a vibrator. Other proprioceptive feedback devices, as known in the art, can also be used.

Figure 2:
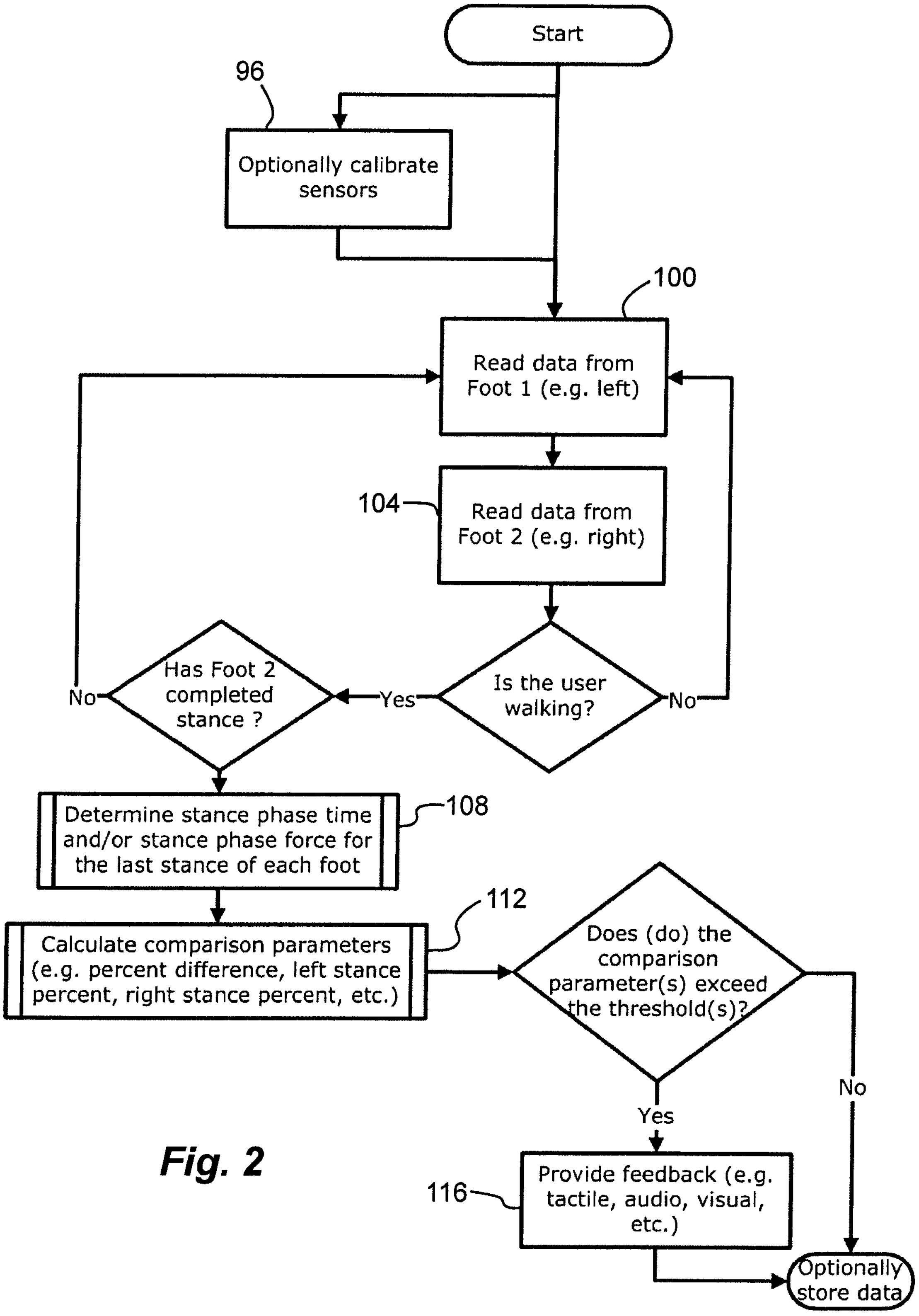
FIG. 2 is a flow chart of a method for analyzing gait and providing real time feedback on gait asymmetry.
Figure 3A:
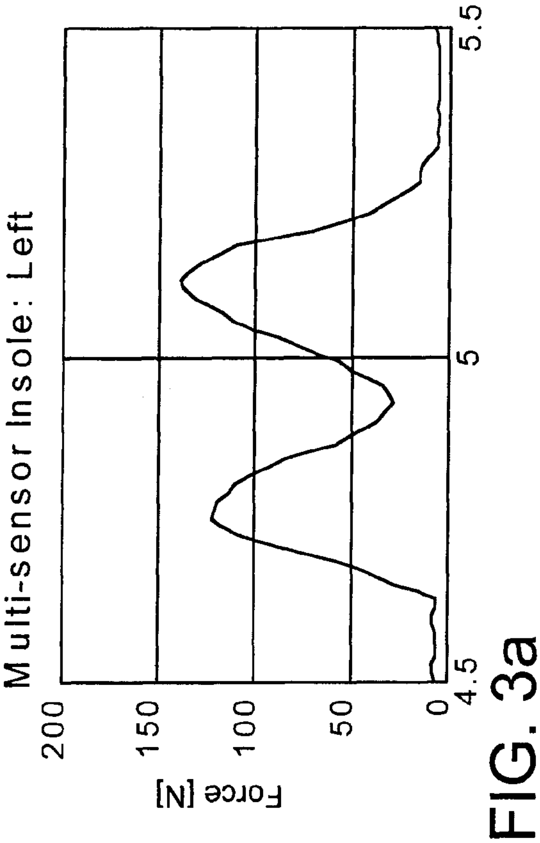
FIG. 3*a* is an exemplary graph of force measure vs. time for stance phase of the left foot.
Figure 3B:
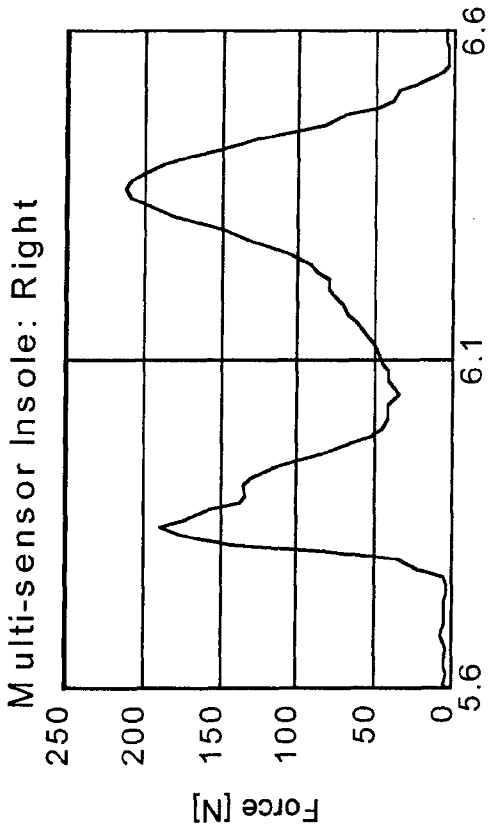
FIG. 3*b* is an exemplary graph of force measure vs. time for stance phase of the right foot.
Figure 3C:
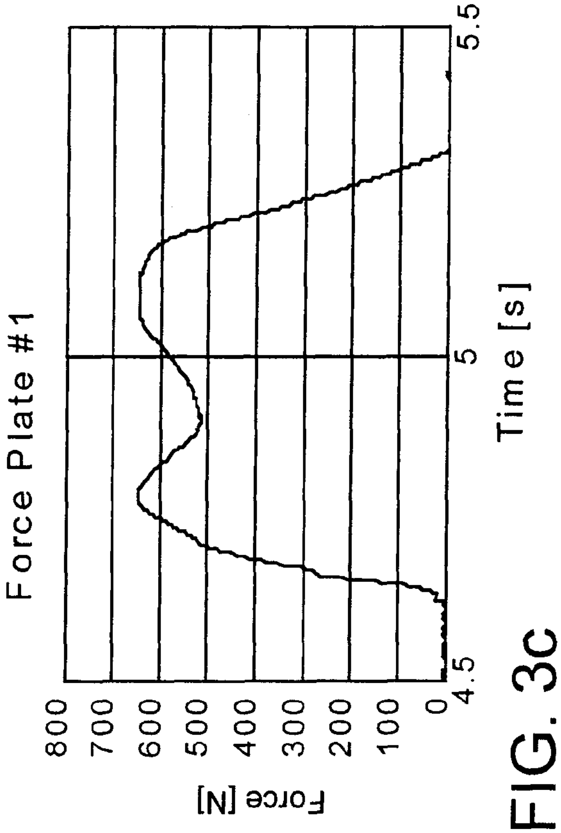
FIG. 3*c* is an exemplary graph of force measure vs. time as measured by a force plate for the left foot.
Figure 3D:
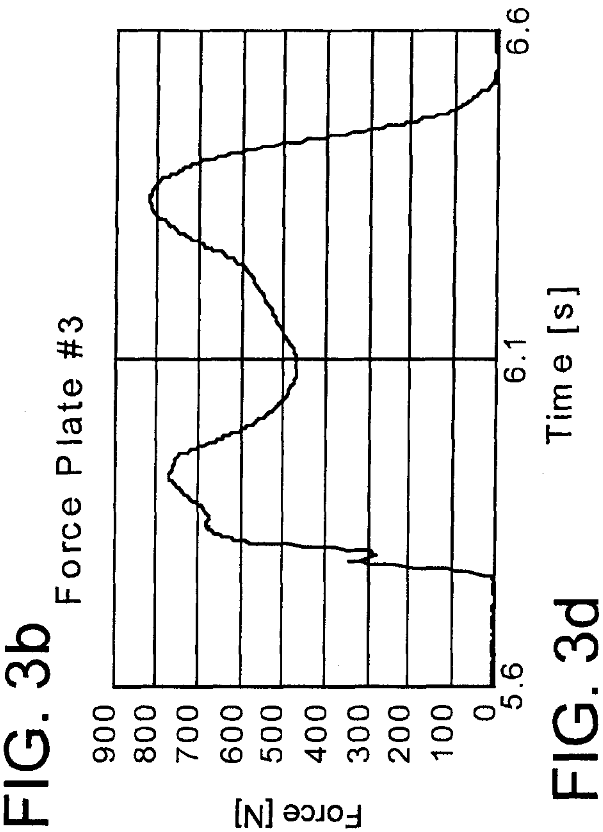
FIG. 3*d* is an exemplary graph of force measure vs. time as measured by a force plat for the right foot.
Figure 4:
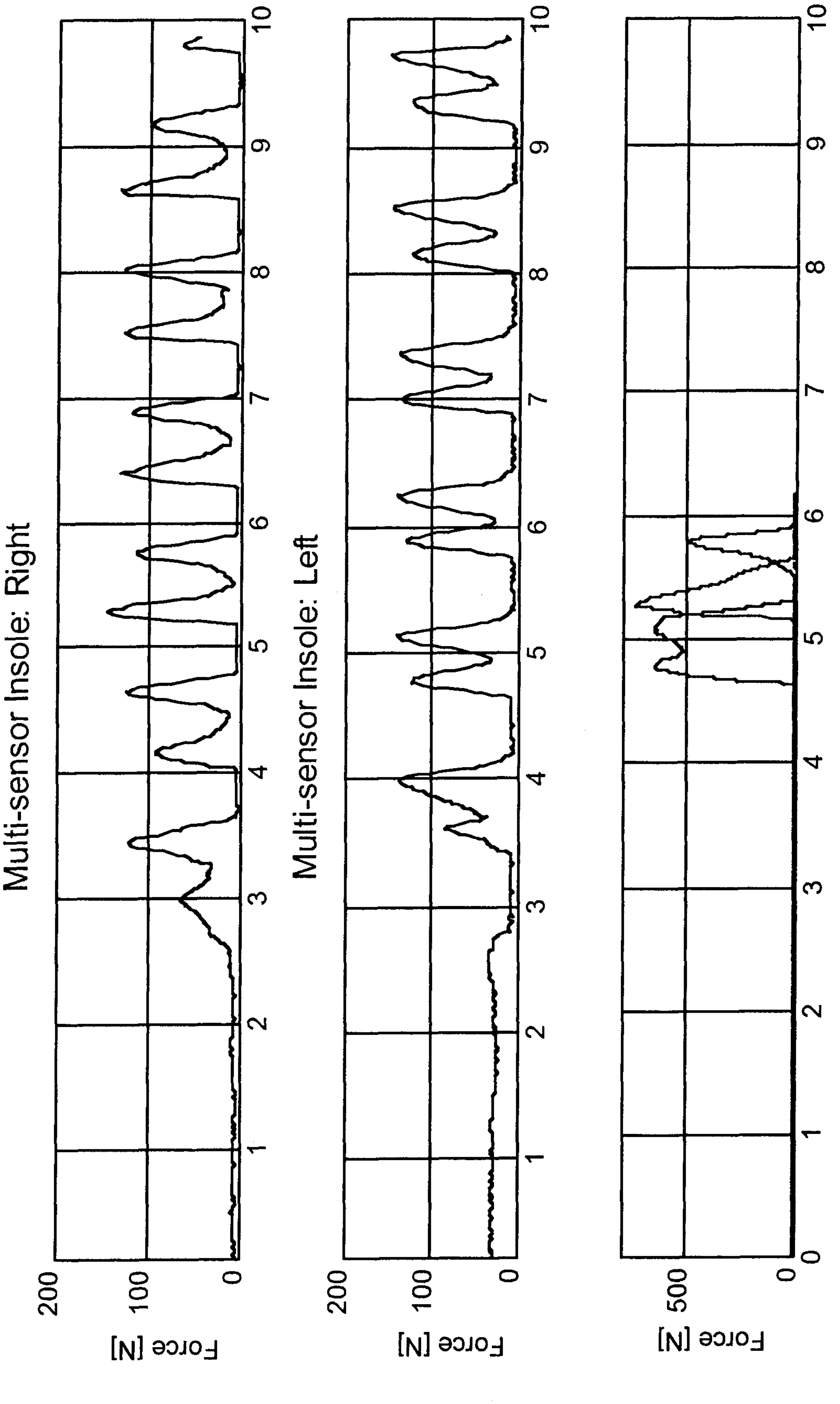
FIG. 4 is exemplary graphs of force measured vs. time for left and right feet through several stance phases and swing phases.

Referring to FIG. 2, the present invention can also include a method for analyzing gait and providing real time feedback on gait asymmetry. Initially, the sensors 40 (FIG. 1) can be calibrated 96. Sensor data is received 100 and 104 from a plurality of sensors disposed within left and right shoes 20 (FIG. 1) when the shoes are moved through gait motions by user of the shoes. In one aspect of the present invention, the sensor data can include force and/or contact data indicative of the force applied during gait motion (FIGS. 3*a* and 3*b*) and contact of the shoe with the walking surface, respectively. The sensor data can be analyzed with an electronic processor by comparing sensor data from one of the shoes to the other of the shoes to determine a difference 108 between the shoes. The processor can also determine the magnitude of force applied between the shoes. In addition, the processor can determine the stance phase time of the shoes. Furthermore, the processor can compare the difference 112 between the stance phase time and/or force between the shoes and a predetermined threshold. Thus, the severity of an asymmetrical gait in the user can be determined. A feedback alarm can be activated 116 to alert the user when the severity of asymmetrical gait exceeds a predetermined threshold.

Receiving sensor data can also include transmitting data from the sensors by a wireless transmitter. The data transmitted by the wireless transmitter can be received by a wireless receiver. The data from the wireless receiver can be routed to the electronic processor.

Analyzing the sensor data can also include comparing stance phase time of one of the shoes with the stance phase time of the other of the shoes (FIGS. 3*a* and 3*b*) in order to determine the stance phase time asymmetry of the user. The total stance phase force applied to one of the shoes can be compared by the electronic processor with the total stance phase force applied to the other of the shoes in order to determine the stance phase force loading asymmetry of the user.

Activating the feedback alarm can also include sounding an audible noise from a speaker when the stance phase time/force applied to one of the pair of shoes varies with respect to the other of the pair of shoes by a predetermined threshold. A first noise can be sounded when stance phase time asymmetry exceeds a predetermined threshold. A second noise can be sounded when the stance phase force loading asymmetry exceeds a predetermined threshold. A third noise can be sounded when both stance phase time asymmetry and stance phase force loading asymmetry together exceed a predetermined threshold. A fourth distinct noise can be sounded for steps taken by the user that fall within the parameters of the predetermined threshold.

The method can also include adjusting the predetermined threshold based on individual calibration data from the user.

It will be appreciated that while the embodiments described herein generally focus on amputees, the concepts of the present invention can be applied to other physiological conditions that can cause an asymmetrical weight distribution on a person's legs. For example, following orthopedic surgery such as a hip replacement, patients often need to initially keep the weight borne on the affected limb underneath a threshold level (e.g. 10% of bodyweight). Overtime, this threshold is increased, and eventually, patients need to be sure to bear full bodyweight. The devices described herein could be used to provide feedback if the patient exceeds the threshold or is not bearing full body-weight.

Furthermore, osteoarthritis may not be the only problem helped by the concepts of the present invention. For example, a unilateral amputee is at great risk of becoming a bilateral amputee due to overloading of the intact limb. Thus, the more symmetric a person's walk and minimizing the impact on a sound limb, the less likely the person will become a bilateral amputee. In addition, there is a strong social motivation for person's with amputations to reduce visible limp.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method for analyzing gait and providing real time feedback on gait asymmetry to a user, comprising:

a) receiving sensor data from a plurality of force sensors and at least one accelerometer disposed within left and right shoes when the shoes are moved through gait motions by a user of the shoes;

b) analyzing the sensor data with an electronic processor located remotely from the plurality of sensors, wherein analyzing the sensor data includes determining and comparing total stance phase forces, the electronic processor analyzing the sensor data by comparing sensor data from the left shoe to the right shoe to determine a difference between the left and right shoes, wherein determining a difference between the left and right shoes includes determining a difference between total stance phase forces; and c) activating a sensory feedback alarm to alert the user when the difference between total stance phase forces or stance phase times of the left and right shoes exceeds a predetermined threshold.

2. A method in accordance with claim 1, wherein analyzing the sensor data further includes:

determining and comparing total stance phase forces or both stance phase times and total stance phase forces of the left and right shoes based on the sensor data and determining a difference between total stance phase forces or both stance phase times and total stance phase forces between the left and right shoes; and wherein activating the sensory feedback alarm further includes:

activating the sensory feedback alarm to alert the user when the total stance phase forces or both stance phase times and total stance phase forces of the left and right shoes exceeds a predetermined threshold.

3. A method in accordance with claim 1, wherein activating the sensory feedback alarm further includes:

sounding an audible noise from a speaker when the difference between the left and right shoes exceeds the predetermined threshold.

4. A method in accordance with claim 3, further comprising adjusting the predetermined threshold based on individual calibration data from the user.

5. A method in accordance with claim 3, wherein activating the sensory feedback alarm further includes:

a) sounding a first alarm when a stance phase time asymmetry between the left and right shoes exceeds a predetermined threshold;

b) sounding a second alarm distinct from the first alarm when a stance phase force asymmetry between the left and right shoes exceeds a predetermined threshold; and c) sounding a third alarm distinct from both the first and second alarms when both the stance phase time asymmetry and stance phase force asymmetry together exceed a predetermined threshold.

6. A method in accordance with claim 1, further comprising:

activating the sensory feedback alarm to sound a distinct alarm for steps taken by the user that fall within parameters of the predetermined threshold.

7. A method in accordance with claim 1, wherein the predetermined threshold is at least 15% difference between the left and right shoes.

8. A method in accordance with claim 1, wherein receiving sensor data from a plurality of sensors disposed within left and right shoes further comprises receiving sensor data from toe sensors in the toe of the shoes and heel sensors in the heel of the shoes.

9. A method in accordance with claim 8, wherein receiving sensor data from a plurality of sensors disposed within left and right shoes further comprises receiving sensor data from sensors disposed in sensor inserts or insoles with the sensor inserts or insoles split between the toe and the heel.

10. A method in accordance with claim 1, wherein receiving sensor data from a plurality of sensors disposed within left and right shoes further comprises receiving sensor data via wireless transmitter and receiver.

11. A method in accordance with claim 1, further comprising determining and comparing stance phase times including determining a time the user applies a force to one of the shoes.

12. A method in accordance with claim 1, further comprising determining and comparing stance phase times including determining a time from initial contact with a ground until final contact with the ground.

13. A method in accordance with claim 1, further comprising determining and comparing stance phase times including determining a time from heel strike to toe off.

14. A method for analyzing gait and providing real time feedback on gait asymmetry to a user, comprising:

a) receiving sensor data from a plurality of force sensors and at least one accelerometer disposed within left and right shoes when the shoes are moved through gait motions by a user of the shoes;

b) determining and comparing total stance phase forces of the left and right shoes with an electronic processor located remotely from the plurality of sensors based on the sensor data and determining a difference between total stance phase forces between the left and right shoes; and c) activating a sensory feedback alarm to alert the user when the difference between total stance phase forces or stance phase times of the left and right shoes exceeds a predetermined threshold.

15. A method in accordance with claim 14, wherein determining a difference between total stance phase forces further includes determining a difference between total stance phase forces in real time during gait motions; and wherein activating the sensory feedback alarm further includes activating the sensory feedback alarm in real time during gait motions.

16. A method in accordance with claim 14, wherein activating the sensory feedback alarm further includes: sounding an audible noise from a speaker when the difference between total stance phase forces of the left and right shoes exceeds the predetermined threshold.

17. A method in accordance with claim 14, further comprising adjusting the predetermined threshold based on individual calibration data from the user.

18. A method in accordance with claim 14, wherein activating the sensory feedback alarm further includes:

a) sounding a first alarm when the difference between stance phase times of the left and right shoes exceeds a predetermined threshold;

b) sounding a second alarm distinct from the first alarm when the difference between stance phase forces of the left and right shoes exceeds a predetermined threshold; and c) sounding a third alarm distinct from both the first and second alarms when the difference between stance phase times and stance phase forces of the left and right shoes together exceed a predetermined threshold.

19. A method in accordance with claim 14, further comprising:

activating the sensory feedback alarm to sound a distinct alarm for steps taken by the user that fall within parameters of the predetermined threshold.

20. A method in accordance with claim 14, wherein the predetermined threshold is at least 15% difference between the left and right shoes.

21. A lower extremity feedback system, comprising:

a) left and right shoes;

b) a plurality of force sensors and at least one accelerometer associated with the shoes;

c) a microcontroller electronically coupled to and located remotely from the plurality of force sensors and the at least one accelerometer and the microcontroller being capable of analyzing data from the force sensors and the at least one accelerometer to determine and compare total stance phase forces of the left and right shoes during gaited motion and to determine a difference between total stance phase forces of the left and right shoes; and d) a sensory feedback device electronically coupled to the microcontroller to sound a sensory alarm when the difference between total stance phase forces or stance phase times of the left and right shoes exceeds a predetermined threshold.

22. A system in accordance with claim 21, wherein the sensory feedback device is selected from the group consisting of: an auditory speaker, a visual indicator, a vibrator, and combinations thereof.

* * * * *